US006969857B2

(12) United States Patent
Owen

(10) Patent No.: US 6,969,857 B2
(45) Date of Patent: Nov. 29, 2005

(54) COMPENSATED INFRARED ABSORPTION SENSOR FOR CARBON DIOXIDE AND OTHER INFRARED ABSORBING GASES

(75) Inventor: Thomas E. Owen, Helotes, TX (US)

(73) Assignees: Southwest Research Institute, San Antonio, TX (US); Gas Research Institute, Des Plaines, IL (US)

( * ) Notice: Subject to any disclaimer, the term of this patent is extended or adjusted under 35 U.S.C. 154(b) by 0 days.

(21) Appl. No.: 10/753,614

(22) Filed: Jan. 8, 2004

(65) Prior Publication Data

US 2004/0206906 A1    Oct. 21, 2004

Related U.S. Application Data

(60) Provisional application No. 60/439,319, filed on Jan. 10, 2003.

(51) Int. Cl.[7] .............................................. G01N 21/35
(52) U.S. Cl. ..................................................... 250/343
(58) Field of Search ........................................ 250/343

(56) References Cited

U.S. PATENT DOCUMENTS

| 3,940,623 | A | * | 2/1976 | Hempowitz et al. ........ 250/343 |
| 5,436,457 | A | * | 7/1995 | Tomita ....................... 250/343 |
| 5,552,841 | A | * | 9/1996 | Gallorini et al. .............. 351/49 |
| 5,646,729 | A |   | 7/1997 | Koskinen et al. ........... 356/352 |

FOREIGN PATENT DOCUMENTS

JP          9-264790 A    *  10/1987    ............. G01J 5/20

OTHER PUBLICATIONS

PCT International Search Report and Written Opinion for US04/00342, 13 pages not a publication.

* cited by examiner

Primary Examiner—Constantine Hannaher
(74) Attorney, Agent, or Firm—Baker Botts L.L.P.

(57) ABSTRACT

A gas sensor, whose chamber uses filters and choppers in either a semicircular geometry or annular geometry, and incorporates separate infrared radiation filters and optical choppers. This configuration facilitates the use of a single infrared radiation source and a single detector for infrared measurements at two wavelengths, such that measurement errors may be compensated.

21 Claims, 1 Drawing Sheet

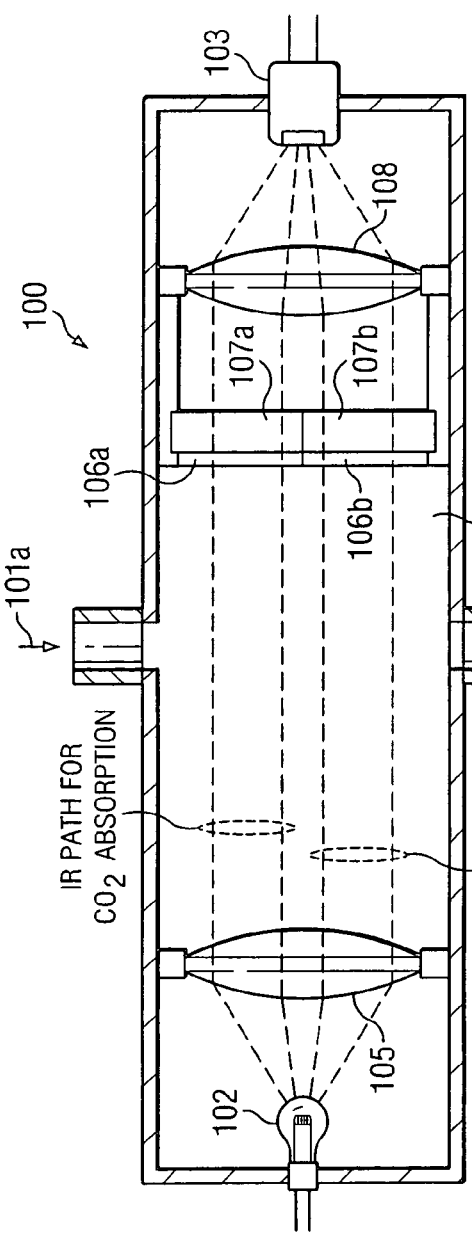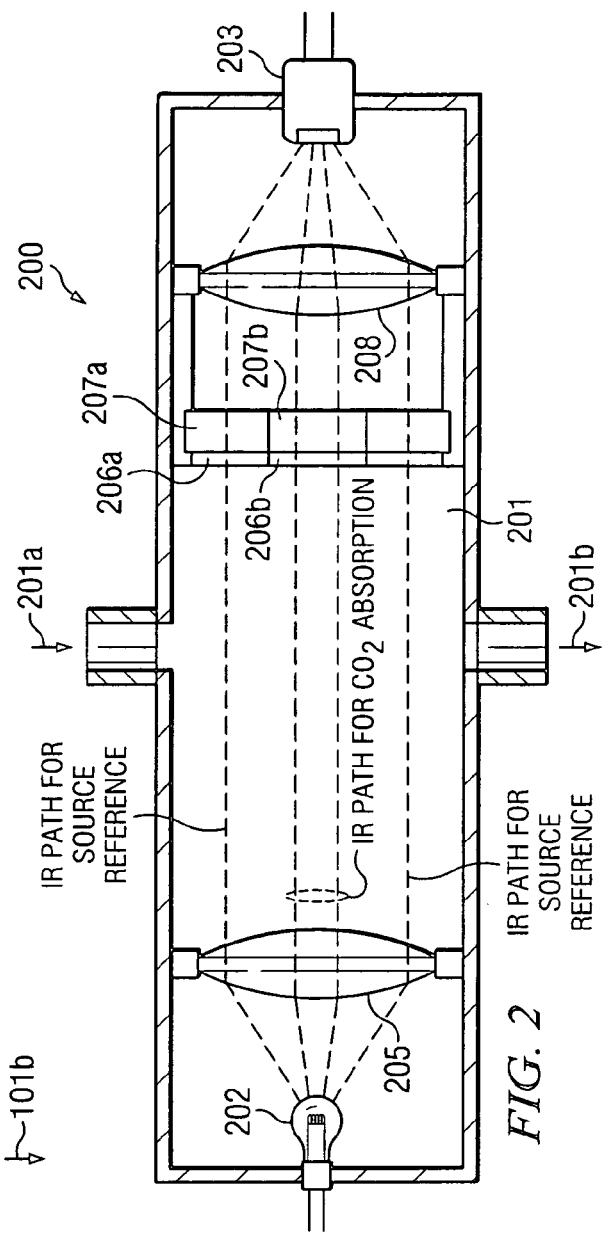

COMPENSATED INFRARED ABSORPTION SENSOR FOR CARBON DIOXIDE AND OTHER INFRARED ABSORBING GASES

RELATED PATENT APPLICATION

This application claims the benefit of U.S. Provisional Application No. 60/439,319, filed Jan. 10, 2003 and entitled "COMPENSATED INFRARED ABSORPTION CARBON DIOXIDE SENSOR".

GOVERNMENT RIGHTS CLAUSE

The U.S. Government has a paid-up license in this invention and the right in certain circumstances to require the patent owner to license others on reasonable terms as provided for by the terms of Contract No. DE-FC21-96MC33033 for the U.S. Department of Energy.

TECHNICAL FIELD OF THE INVENTION

This invention relates to detecting the presence of gas in a gas mixture, and more particularly to an infrared absorption sensor for measurement of the content of carbon dioxide (or other infrared absorbing gas) in a gas mixture.

BACKGROUND OF THE INVENTION

Most gases and vapors exhibit well defined optical spectral absorption bands, in which the transmission of optical energy is absorbed. Carbon dioxide ($CO_2$) has several absorption bands in the infrared optical range. In particular, a predominant absorption band occurs at a wavelength of 4.26 micrometers. This absorption band is relatively sharply defined within a wavelength range of about 4.26 plus or minus 0.2 micrometers. Infrared radiation transmitted through $CO_2$ gas at a wavelength of 4.26 micrometers is strongly attenuated.

The absorption of infrared radiation in a gas occurs at the atomic and molecular level. In the case of $CO_2$, the polyatomic molecular structure determines the photon excitation modes and energy exchange rates, and hence, the wavelengths at which optical energy absorption occurs. Because this absorption effect occurs at the molecular level, the absorption of infrared radiation along a given transmission path depends on the number of molecules present. That is, the amount of absorption at 4.26 micrometers is directly proportional to the molecular fraction of $CO_2$ present in a gas mixture. Additionally, because pressure and temperature affect the density of the gas, the absorption is also dependent on the pressure and temperature at which the infrared absorption measurements are made.

This selective optical absorption phenomena has application as a method for determining the presence and amount of $CO_2$ in samples of gas mixtures. For example, a basic $CO_2$ sensing technique in common use employs an infrared radiation source (typically an incandescent lamp) and an infrared detector (typically a semiconductor photodiode) in a closed chamber in which gas samples are introduced for testing. A narrowband interference filter is used as the optical window of the photodiode detector to make it selective only to the 4.26 micrometer absorbing wavelength. For a given optical path length in the test chamber, the photodetector output can be calibrated using gas mixtures having a known $CO_2$ gas concentration to provide a useful instrument for sensing $CO_2$ in a variety of gas mixtures. The basic sensitivity of this arrangement depends on the sharpness of the interference filter so as to minimize the amount of infrared radiation not related to $CO_2$ absorption reaching the detector, the optical path length containing the $CO_2$ molecules, the luminance stability of the infrared radiation source, and the stability of the detection response of the photodiode detector. Other factors that can affect the sensitivity and calibration accuracy of the method include possible turbulent flow in the gas sample passing through the test chamber, aging of the infrared radiation source and detector, and contamination accumulation on the source and detector optical windows.

The effects of turbulent flow can be minimized, and reliable measurements of gas pressure and temperature can be provided, by proper test chamber design. Other sources of error, such as aging effects on the source intensity and detector sensitivity and non-uniform contamination on the optical windows can be minimized by using the 4.26 micrometer wavelength to sense the absorption of $CO_2$ in the presence of the various error-causing factors and also sensing the infrared intensity incident on the detector at a nearby wavelength, such as at 3.9 micrometers, at which no $CO_2$ absorption occurs. Then, by normalizing the $CO_2$ absorption response to the non-absorbing response, the errors associated with all factors other than the molecular absorption of $CO_2$ can be compensated in the sensor output reading. An example of an error-compensated $CO_2$ sensor is described in U.S. Pat. No. 5,646,729, entitled "Single Channel Gas Concentration Measurement Method and Apparatus Using a Short-Resonator Fabry-Perot Interferometer", issued in 1997 to Koskinen, et al.

BRIEF DESCRIPTION OF THE DRAWINGS

FIG. 1 illustrates a first embodiment of a sensor in accordance with the invention, having a semicircular arrangement of filters and choppers.

FIG. 2 illustrates a second embodiment of a sensor in accordance with the invention, having an annular arrangement of filters and choppers.

DETAILED DESCRIPTION OF THE INVENTION

FIGS. 1 and 2 illustrate two embodiments of a compensated infrared $CO_2$ sensor in accordance with the invention. Both embodiments have two optical paths, but only a single infrared radiation source 102, 202 and a single infrared radiation detector 103, 203. Both embodiments use a pair of fixed optical interference filters 106a/106b, 206a/206b in combination with an optical chopper 108, 208 to achieve separate and independent measurements at 4.26 micrometers and at 3.9 micrometers. By normalizing the 4.26 micrometer absorption measurement with the 3.9 micrometer measurement, aging effects in the infrared source 102 and in the detector 103, and to some extent, the effects of contamination of the optical windows, are compensated.

For purposes of this description, the 4.26 micrometer wavelength is referred to as the "gas attenuating" wavelength. The 3.9 micrometer wavelength is referred to as the "reference" wavelength. It is possible that other wavelengths in the neighborhood of 3.9 micrometers could be used. It is expected that a range of 3.9 micrometers plus or minus 0.1 micrometers could be used. Wavelengths outside that range are undesirable because of interference with the 4.26 micrometer wavelength.

FIG. 1 illustrates a first embodiment of a compensated infrared $CO_2$ sensor 100 in accordance with the invention.

The sensor chamber 101 has an infrared radiation source 102 at one end and an infrared detector 103 at the other. In the example of this embodiment, the radiation source 102 is an incandescent lamp, and the infrared detector 103 is a photodiode. A gas inlet 101a permits chamber 101 to receive gas containing CO2 and a gas outlet 101b is used to exhaust the gas.

Chamber 101 is generally tubular in shape, and in the embodiment of this description has a circular cross sectional area. The interior elements, namely collimator lens 105, filters 106a and 106b, chopper 107, and focusing lens 108 can be made circular in shape to generally conform to the inner diameter of chamber 101. In other embodiments, chamber 101 could have a cross sectional geometry other than cylindrical, such as a rectangular cross section with the interior elements modified in shape accordingly.

Collimator lens 105 collimates the infrared radiation from source 102 and focusing lens 108 focuses the radiation on detector 103. Lenses 105 and 108 are typically sapphire or germanium lenses.

In the example of this description, where chamber 101 is cylindrical, filters 106a and 106b each have a semicircular geometry. One filter filters a first half of the cross-section of the collimated radiation along the length of chamber 101 and the other filter filters the other half of the collimated radiation cross-section. As stated above, one filter is selective to 3.9 micrometer wavelength and the other is selective to 4.26 micrometer wavelength. The effect of filters 106a and 106b is to split the radiation path in half, so that one half comprises 4.26 micrometer wavelength radiation and the other half comprises 3.9 micrometer wavelength radiation.

Choppers 107a and 107b chop the radiation passing through the filters 106a and 106b, respectively. The geometry of choppers 107a and 107b conforms to the geometry of filters 106a and 106b, such that each chopper has a semicircular geometry. Choppers 107a and 107b act as alternating shutters to block and pass the radiation transmitted through the filters 106a and 106b. They operate sequentially such that detector 103 sequentially and periodically receives a reference signal from filter 107a and a CO2-attenuated signal from filter 107b (or vice versa).

Choppers 107a and 107b are implemented with liquid crystal devices (LCDs), and perhaps most conveniently as a two-section liquid crystal chopper. For example, an LCD array could be used such that its top portion is used to chop the radiation from filter 106a and its bottom portion is used to chop the radiation from filter 106b. The two portions are thus independently operable.

The use of liquid crystal choppers eliminates the need for a mechanical rotating disk chopper. Various commercially available liquid crystal compounds, such as Lixon 5005 or Lixon 5018 manufactured by the Chisso Company, Ltd., combined with appropriate infrared optical polarizer components may be used to form electrically driven LCD light modulator devices adaptable for use as choppers 107a and 107b, provided that they are suitable for transmitting and blocking the particular infrared radiation wavelengths of interest.

Conventional electronic circuitry and processing devices (not shown) may be used to control choppers 107a and 107b and to normalize the 4.26 micrometer signal by the 3.9 micrometer signal. The attenuation of the signal through chopper 107b depends on the amount of CO2 present in the optical path within chamber 101.

FIG. 2 illustrates a second embodiment of a compensated infrared CO2 sensor 200 in accordance with the invention. Like sensor 101, its sensor chamber 201 has a single infrared radiation source 202 and a single infrared detector 203.

Chamber 201, and its inlet 201a and outlet 201b are essentially the same as those of sensor 101. Likewise, collimator lens 205 and focusing lens 208 are the same.

Filter 206a has an annular geometry and filter 206b has a circular geometry. The annular geometry of filter 206b generally forms a collar extending into the inner diameter of chamber 201. The circular geometry of filter 206b fills the middle of the ring formed by filter 206a. As a result of the configuration of filters 206a and 206b, filter 206a filters an outer ring of the collimated radiation along the length of chamber 201 and filter 206b filters an inner beam of the radiation. One filter is selective to a 3.9 micrometer wavelength and the other is selective to 4.26 micrometer wavelength.

Choppers 207a and 207b chop the radiation transmitted from filters 206a and 206b, respectively. The geometry of choppers 207a and 207b conforms to the geometry of filters 206a and 206b, such that chopper 207b is annular and chopper 206b is circular.

In other words, the geometry of the filters and chopper of the embodiment of FIG. 2 is "annular" in the sense that an inner portion of the filters and the chopper operate on an inner portion of the beam of infrared radiation and an outer portion of the filters and the chopper operate on an outer portion of the beam of infrared radiation. If chamber 201 were to have a rectangular cross section rather than circular, the same geometry would apply such that an inner rectangular area (rather than an inner circular area) would be filtered and chopped differently from an outer rectangular area.

In contrast, the geometry of the filters and chopper of the embodiment of FIG. 1 is "split", in the sense that a first portion of the filters and the chopper operate on a first side of the beam of infrared radiation and a second portion of the filters and the chopper operate on a second of the beam of infrared radiation. The split geometry could be two halves of a circle or two sides of a rectangular, depending on the inner cross sectional geometry of chamber 101.

The size of both embodiments described above can be quite small. The infrared sources 102 and 202 and the detectors 103 and 203 can be "grain of wheat" sized devices. The overall dimensions of sensors 100 and 200, assuming they are cylindrical in shape, could be as small as ½ inch in diameter and 1 inch in length.

In both embodiments described above, the normalized output signal from the sensor is independent of any changes in the common infrared source and photodiode detector used in the alternating measurements. Also, because the lenses and filters are relatively small, their surfaces will tend to accumulate uniformly distributed contamination on their surfaces.

In the above-described embodiments, each pair of filters (106a/106b and 206a/206b) intercepts approximately half of the radiation from the associated radiation source. In other words, their surface areas are equal. Also, the filters are placed adjacent each other so that they each intercept a portion of the radiation within chamber 101 or 201 at the same distance from the radiation source 102. In the embodiments of FIGS. 1 and 2, they are in the same plane across the cross sectional area of the chamber. This is the simplest and most direct approach to normalization of the signal. However, filters having different surface area sizes and placements may also be used.

Although the description above is directed to CO2 sensing, especially in natural gas, the same concepts could be applied to detect other gases that absorb infrared radiation and other gas mixtures. For example, the presence of water vapor or gaseous ammonia could be detected using their appropriate infrared absorption wavelengths.

What is claimed is:

1. A sensor for detecting an infrared absorbing subject gas in a gas mixture, comprising:
    a sensor chamber being generally in the shape of a hollow tube;
    an infrared radiation source at a first end of the sensor chamber, operable to generate a beam of infrared radiation along the length of the chamber;
    a first filter operable to receive a portion of the beam of infrared radiation and passing a wavelength of radiation known to be attenuated by transmission through the subject gas;
    a second filter operable to receive a second portion of the beam of infrared radiation and passing a wavelength of radiation known to be not significantly attenuated by transmission through the subject gas;
    wherein the filters are arranged immediately adjacent each other to form a cross-sectional closed-shaped geometry having an inner filter and an outer filter;
    a chopper operable to selectively and in succession block and pass radiation from the first filter and the second filter, the chopper comprising a stationary array of light modulating elements that are controllable in two sections to alternately block and pass the radiation;
    wherein the sections of the array have the same geometry as the inner and outer filter; and
    an infrared detector for detecting radiation passed through the chopper.

2. The sensor of claim 1, wherein the geometry is generally circular.

3. The sensor of claim 1, wherein the geometry is generally rectangular.

4. The sensor of claim 1, wherein the outer portion is annular relative to the inner portion.

5. The sensor of claim 1, wherein the filters are equidistant from the infrared radiation source.

6. The sensor of claim 1, wherein the first filter is sensitive to a wavelength that attenuates radiation through carbon dioxide.

7. The sensor of claim 1, wherein the second filter is sensitive to a wavelength of about 3.9 micrometers.

8. The sensor of claim 1, wherein the first filter is sensitive to a wavelength that attenuates radiation through water vapor.

9. The sensor of claim 1, wherein the first filter is sensitive to a wavelength that attenuates radiation through gaseous ammonia.

10. The sensor of claim 1, wherein the radiation source is an incandescent source.

11. The sensor of claim 1, further comprising a collimating lens operable to receive the beam of infrared radiation from the source and to collimate the radiation within the beam.

12. The sensor of claim 1, further comprising a focusing lens operable to focus the beam of infrared radiation to the detector.

13. The sensor of claim 1, wherein each filter receives substantially a one half portion of the beam of infrared radiation.

14. The sensor of claim 1, wherein the chopper is implemented with at least one liquid crystal device.

15. A method of detecting an infrared absorbing subject gas in a gas mixture, comprising:
    generating a beam of infrared radiation with a light source;
    filtering a first portion of the beam of infrared radiation, using a first filter, which passes a wavelength of radiation known to be attenuated by transmission through the subject gas;
    filtering a second portion of the beam of infrared radiation, using a second filter, which passes a wavelength of radiation known to not be significantly attenuated by transmission through the subject gas;
    wherein the filters are arranged immediately adjacent each other to form a cross-sectional polygon-shaped geometry having an inner filter and an outer filter;
    wherein the filters are equidistant from the light source;
    using a chopper to selectively and in succession block and pass radiation from the first and second filters, the chopper comprising a stationary array of light modulating elements that are controllable in two sections to alternately block and pass the radiation;
    wherein the sections of the array have the same geometry as the inner and outer filter; and
    detecting radiation passed through the chopper.

16. The method of claim 15, wherein the first filter is sensitive to a wavelength that attenuates radiation through carbon dioxide.

17. The method of claim 15, wherein the second filter is selective to a wavelength of about 3.9 micrometers.

18. The method of claim 15, wherein the first filter is sensitive to a wavelength that attenuates radiation through water vapor.

19. The method of claim 15, wherein the first filter is sensitive to a wavelength that attenuates radiation through gaseous ammonia.

20. The method of claim 15, wherein each filter receives substantially a one half portion of the beam of infrared radiation.

21. The method of claim 15, wherein the chopper is implemented with at least one liquid crystal device.

* * * * *